(12) United States Patent
McKay (10) Patent No.: US 10,588,678 B2
(45) Date of Patent: Mar. 17, 2020

(54) FILTRATION DEVICE

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 404 days.

(21) Appl. No.: 15/149,890

(22) Filed: May 9, 2016

(65) Prior Publication Data

US 2016/0249966 A1 Sep. 1, 2016
US 2019/0000522 A9 Jan. 3, 2019

Related U.S. Application Data

(62) Division of application No. 13/655,500, filed on Oct. 19, 2012, now Pat. No. 9,333,447.

(51) Int. Cl.
*A61B 17/88* (2006.01)
*B01D 33/01* (2006.01)
*G06F 16/958* (2019.01)
*A61F 2/28* (2006.01)

(52) U.S. Cl.
CPC ............ *A61B 17/8833* (2013.01); *A61F 2/28* (2013.01); *B01D 33/0158* (2013.01); *G06F 16/972* (2019.01); *A61F 2002/2835* (2013.01)

(58) Field of Classification Search
None
See application file for complete search history.

(56) References Cited

U.S. PATENT DOCUMENTS

| 5,238,003 | A | 8/1993 | Baidwan et al. |
|---|---|---|---|
| 6,423,237 | B1 | 7/2002 | Guirguis |
| 9,333,447 | B2 * | 5/2016 | McKay ............. B01D 33/0158 |
| 2008/0081367 | A1 | 4/2008 | Sowemino-Coker et al. |
| 2009/0294385 | A1 | 12/2009 | Tajima et al. |
| 2010/0108621 | A1 | 5/2010 | Zainiev |
| 2014/0110356 | A1 * | 4/2014 | McKay ............. B01D 33/0158 210/780 |
| 2016/0249966 | A1 * | 9/2016 | McKay ............. G06F 17/30893 210/767 |
| 2016/0333305 | A1 * | 11/2016 | Pilkington ........... C12N 5/0653 |
| 2017/0368226 | A1 * | 12/2017 | Pilkington ........... B01D 17/047 |
| 2018/0339248 | A1 * | 11/2018 | Chung .................. B01D 33/01 |
| 2019/0000522 | A9 * | 1/2019 | McKay ................ G06F 16/972 |

* cited by examiner

*Primary Examiner* — Robert J Popovics (57) ABSTRACT

A device for separating particulate matter (e.g., cells) from a liquid including a housing defining an elongate chamber disposed between a receiving end and a dispenser end, a plunger slidably inserted within the chamber from the receiving end, an upper disc and a lower disc each independently slidably affixed to the plunger, the lower disc facing the dispenser end and including at least one filter arrangement, and a liquid including particulate matter disposed within the chamber when the upper disc and lower disc are in an aspiration mode. The upper disc is independently slidable with respect to the lower disc to achieve a filtration mode.

9 Claims, 3 Drawing Sheets

FILTRATION DEVICE

This application is a divisional application of U.S. patent application Ser. No. 13/655,500 filed on Oct. 19, 2012. This entire disclosure is incorporated herein by reference into the present disclosure.

BACKGROUND

Bone is a composite material that contains impure hydroxyapatite, collagen and a variety of non-collagenous proteins, as well as embedded and adherent cells. Due to disease, a congenital defect or an accident, a person may lose or be missing part or all of one or more bones or regions of cartilage in his or her body, and/or have improper growth or formation of bone and/or cartilage.

That an organism is missing part of a bone or has a defect is not necessarily a permanent condition, and there are known means by which to address some of these conditions. For example, mammalian bone tissue is known to contain one or more proteinaceous materials that are active during growth and natural bone healing. These materials can induce a developmental cascade of cellular events that results in bone formation. Typically, the developmental cascade of bone formation involves chemotaxis of mesenchymal cells, proliferation of progenitor cells, differentiation of cartilage, vascular invasion, bone formation, remodeling and marrow differentiation. Thus, the control or use of this already existing system can be advantageous when seeking to regenerate or to repair bone.

Often times an allograft material can be used to aid in bone growth and repair of the bone defect. To enhance bone growth, the allograft can be seeded or hydrated with nucleated cells (e.g., white blood cells, red blood cells, progenitor cells, stem cells, etc.) often obtained from blood or bone marrow aspirates. It is desirable to have these nucleated cell types concentrated in the delivery liquid so they can easily be delivered to the allograft material.

Sometimes, it can be difficult to concentrate the cells in the fluid it is obtained from unless laboratory facilities are used. For example, when separating or removing cells from liquid, a filter is used. However, some filters do not easily let the cells through them and may require the use of a centrifuge. Further, because the centrifuge spins the liquid at high speeds, it can damage the nucleated cells causing them to be ineffective when they are added to the allograft material.

When using a centrifuge, installing the sample holding container assemblies in the centrifuge can only be done manually, making it difficult to automate a series of operations including preprocessing. Further, the speed of the centrifuge is the only parameter that can be controlled, which makes fine motor control of the device impossible. Still another problem is that an appropriate centrifugal force needs to be set according to liquid volumes and filter pore diameters, making the equipment difficult to handle.

It is therefore desirable to provide a filtration device and method, which can filter and concentrate cells from or in a liquid conveniently and with a simple construction.

SUMMARY

The current device and method allow concentration of cells in a liquid easily and efficiently at the point of care. The current device and method avoids the need for expensive and extensive laboratory equipment to filter cells. In some embodiments, the device and method provided allow concentrated cells (e.g., white blood cells, red blood cells, progenitor cells, stem cells, etc.) to be obtained from blood or bone marrow aspirates. These nucleated cell types can be concentrated in the delivery liquid so they can easily be delivered to the allograft material to enhance bone growth at the bone defect site.

In one embodiment, a filtration device is provided comprising: a housing defining a chamber disposed between a receiving end and a dispenser end; a plunger slidably inserted within the chamber from the receiving end; a first disc slidably affixed to the plunger; and a second disc slidably affixed to the plunger below the first sliding disc and facing the dispenser end, the second disc including at least one filter arrangement.

In another embodiment, a device for separating particulate matter from a liquid is provided comprising: a housing defining an elongate chamber disposed between a receiving end and a dispenser end; a plunger slidably inserted within the chamber from the receiving end; an upper disc and a lower disc each independently slidably affixed to the plunger, the lower disc facing the dispenser end and including at least one filter arrangement; a liquid including particulate matter disposed within the chamber when the upper disc and lower disc are in an aspiration mode; and a removable cap affixed to the dispensing end, wherein the lower disc is independently slidable with respect to the upper disc to achieve a filtration mode when the cap is affixed to the dispensing end.

In yet another embodiment, a method for separating particulate matter from a liquid is provided comprising the steps of: providing a housing defining an elongate chamber disposed between a receiving end and a dispenser end; providing a plunger slidably inserted within the chamber from the receiving end; providing an upper disc and a lower disc each independently slidably affixed to the plunger, the lower disc facing the dispenser end and including at least one filter arrangement; sliding the upper and lower discs upwards towards the receiving end for aspirating a liquid including particulate matter within the chamber; affixing a cap to the dispensing end; sliding the lower disc downwards to achieve a filtration mode for separating the particulate matter from the liquid; removing the cap; and sliding the upper disc downwards to achieve a concentrated cell expulsion mode.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent.

Reference will now be made in detail to certain embodiments of the application, examples of which are illustrated in the accompanying drawings. While the application will be described in conjunction with the illustrated embodiments, it will be understood that they are not intended to limit the application to those embodiments. On the contrary, the application is intended to cover all alternatives, modifications, and equivalents, which may be included within the application as defined by the appended claims.

The headings below are not meant to limit the disclosure in any way; embodiments under any one heading may be used in conjunction with embodiments under any other heading.

Filtration Device

The current devices and methods allow concentration of cells in a liquid easily and efficiently at the point of care. The current devices and methods avoid the need for expensive and extensive laboratory equipment to filter cells. In some embodiments, the devices and methods provided allow concentrated cells (e.g., white blood cells, red blood cells, progenitor cells, stem cells, etc.) to be obtained from blood or bone marrow aspirates. These nucleated cell types can be concentrated in the delivery liquid so they can easily be delivered to the allograft material to enhance bone growth at the bone defect site. Advantageously, a filtration device comprising a specialized syringe according to various embodiments greatly improves ease of use by enabling easy and quick preparation of a concentrated liquid of particles such as cells, with a minimum number of steps and equipment.

In various embodiments, a filtration device is provided which may be manually operated and comprises a housing including an elongate chamber disposed between a top end and a bottom end. The top end comprises an opening adapted for receiving a plunger, and the bottom end comprises a dispenser end. A removable cap may be provided affixable to the dispenser end of the housing for providing an airtight seal of the dispenser end. Further, a needle or cannula may be provided connectable to the dispenser end via, e.g., a luer lock. In various embodiments, the plunger includes at least a first disc and a second disc each affixed to the plunger and adapted for slidable movement within the chamber along a longitudinal axis. The first disc may comprise a solid disc-shaped member and is configured to move in at least an upward direction toward the top end. The first disc can move dependently or independently of the second disc and/or plunger. The first disc can be non-porous and prevent or inhibit fluid from moving through it and can comprise plastic, rubber and/or another polymer that is impervious to liquids. The second disc is affixed to the plunger below the first disc, e.g., facing the dispenser end, and may include a filter arrangement. The second disc is semi-permeable or permeable to liquids. Thus, the second disc allows all or a portion of the liquid to pass through it and the filter. The second disc and/or filter may move dependently or independently of the first disc and/or plunger. Alternatively, the plunger, the first disc, the second disc and/or filter may be moved in unison in either the upwards toward the top end or downwards directions toward the dispensing end.

According to various embodiments, the plunger may be deployed downwards to push the first and second discs towards the dispenser end to achieve a starting position, and the device may be positioned to insert the dispenser end into a desired fluid liquid for aspiration. The plunger may be pulled upwards to pull the first and second discs towards the top end, thus pulling the liquid into the chamber of the device. A cap is connected to the dispenser end, and the plunger may be pressed downwards to push the second disc towards the dispenser end, thus forcing the liquid through the second disc into an upper compartment dynamically formed between the first and second discs. Particulate matter (e.g., cells) is caused to be filtered out and remains in a lower compartment formed between the dispenser end and the second disc. Once a desired volume of concentrated liquid/cells is achieved in the lower compartment, the cap may be removed and the plunger may be pressed downwards to eject the concentrated cells from the dispenser end for administration to a patient.

Figure 1:
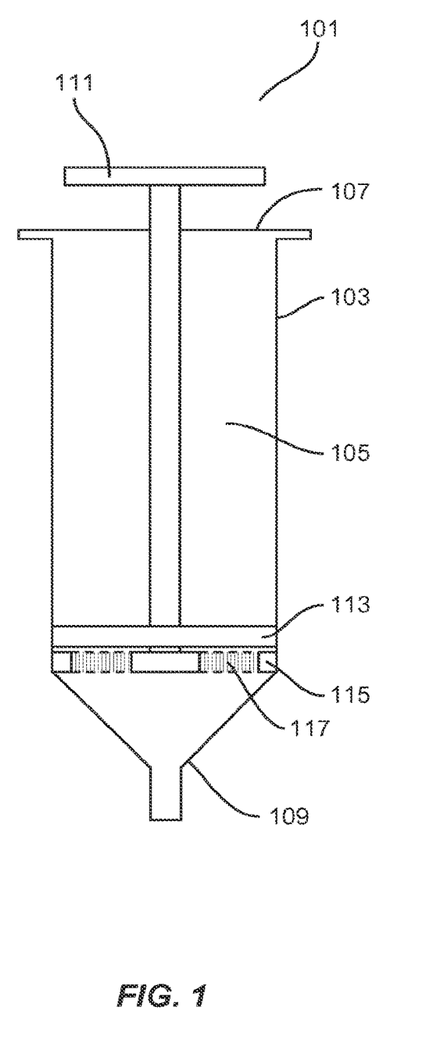
FIG. 1 illustrates a cross-sectional view of an exemplary filtration device according to an aspect of the present application.

FIG. 1 illustrates a cross-sectional view of an exemplary filtration device 101 depicted in a 'starting mode', or position ready for aspiration of fluid, according to an aspect of the present application. The device 101 comprises a housing 103 having a receiving end 107 for receiving a plunger 111 and a dispenser end 109 which may in some embodiments comprise a conical shape having a tip through which fluid may be aspirated or expelled. The housing 103 may comprise e.g., a hollow cylindrical or tubular body defining an elongate chamber 105. The plunger 111 may comprise an elongate rod having a handle at a first end, and is of a length at least sufficient to be insertable within a depth of the chamber 105.

A first or upper disc 113 having an annular shape and periphery which is dimensioned to form a sliding seal with the walls of the chamber 105 may be provided slidably affixed to the plunger 111. In various embodiments, the first disc 113 may be oriented to face the receiving end 107 and forms an airtight seal with respect to the sidewalls of the chamber 105 and the plunger 111 so as to prevent air or fluid flow between the receiving end 107 and the dispenser end 109. The first disc 113 may be formed of any solid or substantially solid, non-porous rigid material, such as plastic, metal, rubber, or similar materials.

Figure 6:
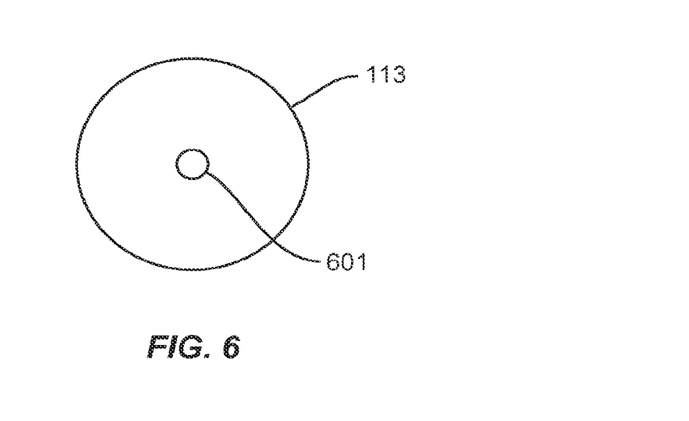
FIG. 6 illustrates a top view of an upper disc according to an aspect of the present application.

FIG. 6 illustrates a top view of an exemplary upper disc according to an aspect of the present application. The upper disc 113 may include a hole 601 adapted for slidably receiving the elongate rod of the plunger there through in a manner which maintains the airtight seal between the receiving end 107 and the dispenser end 109.

The plunger 111 may further include a second or lower disc 115 having an annular shape and periphery which is also dimensioned to form a sliding seal with sidewalls of the chamber 105. The second disc 115 is slidably affixed to the plunger 111 below the first disc 113 so that it faces the dispenser end 109.

In various embodiments, the second disc 115 may include at least one filter arrangement 117 each comprising one or more types and/or layers of filter media or porous media suitable to prevent the passage of matter, such as particulate matter, there through. The nature and properties of the filter or porous media or material may be selected and configured as necessary to provide a desired pore size/density suitable to prevent the passage of particulate matter which is desired to be captured or concentrated.

Figure 5:
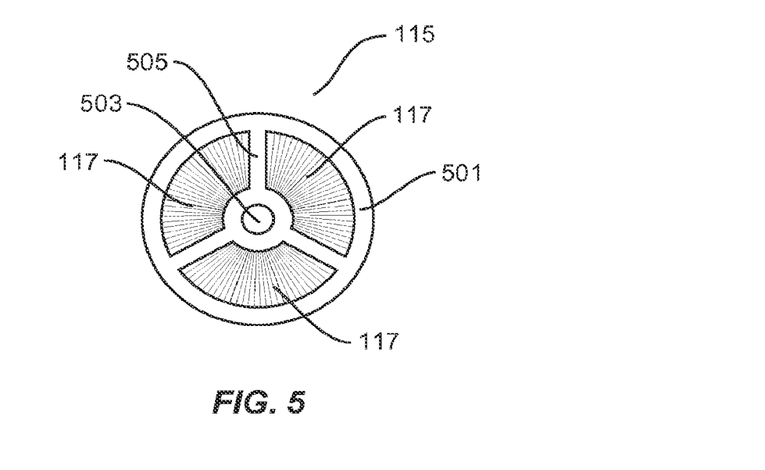
FIG. 5 illustrates a top view of a lower disc according to an aspect of the present application.

FIG. 5 illustrates a top view of an exemplary lower disc 115 including filter arrangements 117 according to an aspect of the present application. In various embodiments, the lower disc 115 may comprise a frame 501 having an annular periphery and a central hole 503 adapted for receiving the plunger 111. The frame 501 comprises any solid, non-porous rigid material and may include a plurality of arms 505 defining at least one void at or within which the at least one filter arrangement 117 may be disposed. The plurality of arms 505 may comprise any number or design, and in some embodiments, advantageously imparts stability to the second disc 115 for supporting the filter arrangements 117 especially during a 'filtration mode' when liquid is caused to flow there through, as discussed further below. In various embodiments, the periphery of the frame 501 is adapted to maintain a slidable airtight seal with the walls of the chamber 105, while allowing liquid to flow through the filter arrangements 117. For example, the filter arrangement can be continuous throughout the frame and comprise recesses and/or projections complementary to the lower disc such that the filter arrangement can fit within the lower disc. In alternative embodiments, the filter arrangement and the lower disc are one piece. In some embodiments, the filter arrangement 117 is disposed within, above or below the at least one void. In various embodiments, the filter arrangements 117 rest on and/or is attached to the top or bottom of arms 505 such that the filter arrangement is a complete circular filter supported by arms 505 as fluid is pushed through the filter arrangement.

The depiction shown in FIG. 5 is for exemplary purposes only and any shape, location, number, configuration and orientation of the filter arrangements 117 may be contemplated. In various embodiments, alternate designs of the frame 501 and filter arrangements 117 may be contemplated to provide for example, desired flow and filtration characteristics.

In various embodiments, the first and second discs 113, 115 are independently slidably affixed to the plunger 111, that is, to enable both independent movement of each disc 113, 115 in an upwards or downwards direction, and their movement in unison in an upwards or downwards direction. This enables the various modes (e.g., 'start mode,' 'aspiration mode,' 'filtration mode,' and 'concentrated cell expulsion mode') to be achieved, as described herein and further below.

Figure 2:
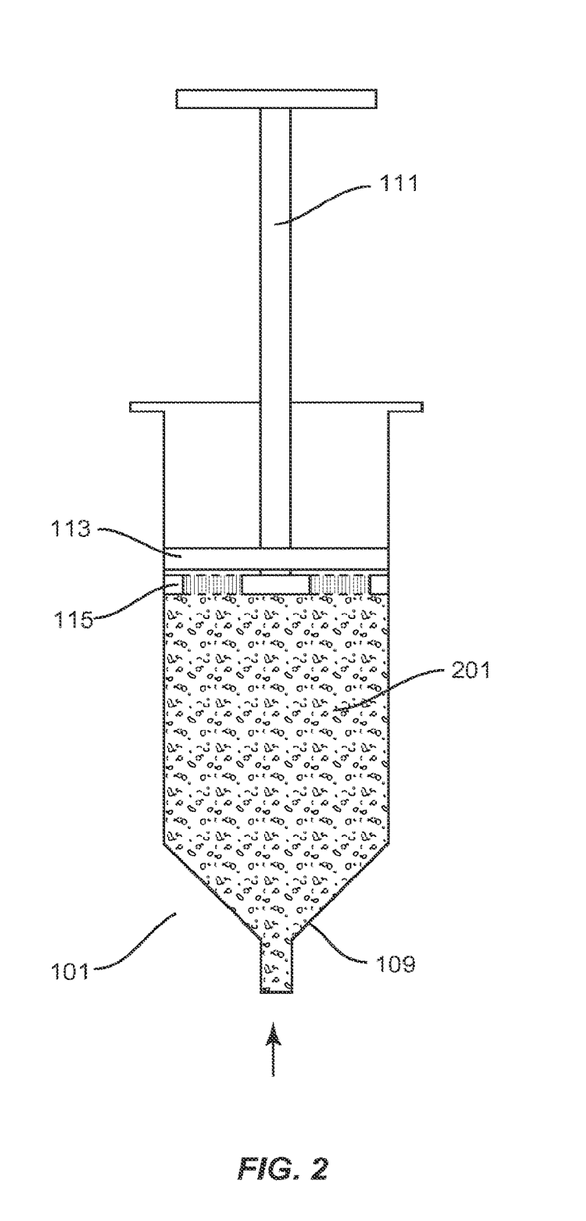
FIG. 2 illustrates a cross-sectional view of the exemplary filtration device of FIG. 1 in a liquid aspiration mode according to an aspect of the present application.

FIG. 2 illustrates a cross-sectional view of the exemplary filtration device of FIG. 1 in an 'aspiration mode' according to an aspect of the present application. In operation, the device 101 allows for the drawing of liquid within the chamber 105 by positioning the plunger 111 and discs 113, 115 proximate to the dispenser end 109 as shown in FIG. 1, immersing the dispenser end 109 into a liquid, and withdrawing the plunger 111 and both discs 113, 115 upwards to a position in the chamber 105 which will cause aspiration of the desired volume of liquid 201 into the chamber 105, for example, as shown in FIG. 2.

In various embodiments, the liquid may comprise any bodily fluid (e.g., blood, aspirate fluid, cerebral fluid, spinal fluid, plasma, marrow, etc.) that includes cells (e.g., eukaryotic cells, white blood cells, red blood cells, progenitor cells, stem cells, etc.) in it including, which are desired to be separated from the liquid. In the aspiration mode in FIG. 2, the dispensing end has the cap off and cells and liquid are drawn into the syringe chamber. Disc 113 and 115 can contact each other and the plunger is drawn up the syringe chamber to the top end so that the liquid including cells fills the syringe chamber.

Figure 3:
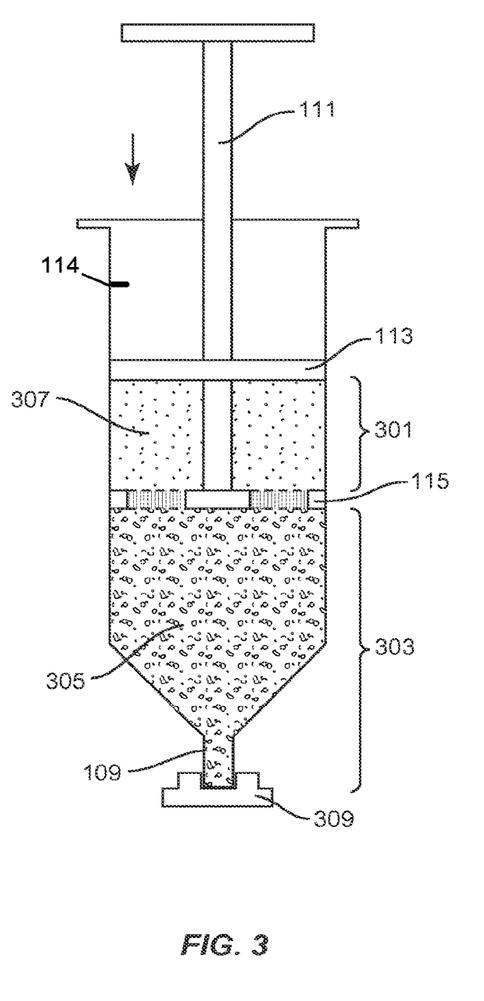
FIG. 3 illustrates a cross-sectional view of the exemplary filtration device of FIG. 2 in a filtration mode according to an aspect of the present application.

In various embodiments, during aspiration of liquid into the chamber 105, the positions of the first and second discs 113, 115 are maintained adjacent to one another. Once the desired amount of liquid is pulled into the chamber 105, a removable cap 309 in FIG. 3 is affixed to the dispenser end 109. The cap 309 may comprise any non-porous material adapted to achieve and maintain an airtight seal with the tip 109. In some embodiments, the cap, syringe, plunger, filter, and/or discs can comprise polyurethane, polyurea, polyether (amide), PEBA, thermoplastic elastomeric olefin, copolyester, and styrenic thermoplastic elastomer, steel, aluminum, stainless steel, nitinol, titanium, metal alloys with high non-ferrous metal content and a low relative proportion of iron, carbon fiber, glass fiber, plastics, ceramics or combinations thereof.

FIG. 3 illustrates a cross-sectional view of the exemplary filtration device 101 of FIG. 2 in a filtration mode according to an aspect of the present application.

In FIG. 3, once the cap 309 is secured, the device may be caused to commence a 'filtration mode' in which the plunger 111 is pressed downwards towards the dispensing end 109 to cause the second disc 115 to move downward towards the dispenser end 109. In this aspect, the liquid will pass through the filter of the second or lower disc 115. The pressure generated by the downward force of the plunger 111 on the liquid (e.g., blood, aspirate fluid, cerebral fluid, spinal fluid, plasma, marrow, etc.) that includes cells (e.g., eukaryotic cells, white blood cells, red blood cells, progenitor cells, stem cells, etc.) will cause the fluid portion 307 of the sample to be separated and passed through the filter, while the cells 305 will be separated by being retained by the filter. Lower compartment 303 will contain a higher concentration of cells in a smaller amount of liquid than in upper compartment 301. The pressure from liquid passing through the second or lower disc 115 and filter will cause the first or upper disc 113 to move in an upward direction away from the dispensing end. Upper compartment 301 will contain predominately fluid 307 and little or no cells. While lower compartment 303 will contain a high concentration of cells 305 and very little fluid.

In operation, the downward movement of the lower or second disc 115 subjects the liquid 307 to pressure and dynamically creates an upper compartment 301 situated between the first disc 113 and the lower disc 115. In some embodiments, the first or upper disc 113 can comprise a recess or projection complementary to the syringe on one or both sides of the disc or portion 114 of the chamber of the syringe can comprise a recess or projection that the upper disc 113 can not slide above. In this way, fluid will not travel above the first or upper disc 113 so that no fluid can leak out of the syringe at its upper end. This recess and/or projection locks the upper disc 113 in position and keeps it there so that it can not go above it. However, the upper disc 113 can slide below it.

In some embodiments, there is a plurality of recesses and/or projections 114 that can be in the syringe chamber 105 that allows the upper disc to be locked in place so that it can not move above or below a certain position in the syringe chamber. In this way, the cells can easily be expelled from the syringe by downward movement of the plunger and the upper disc will not move to any substantial extent in this embodiment.

In some embodiments, as the lower disc 115 is pushed down, the liquid 307 is caused to flow through the filtration arrangement of the lower disc 115 into the upper compartment 301. The filtration arrangement allows for filtered liquid or filtrate 307 to pass through into the upper compartment 301 while substantially preventing particulate matter (e.g., cells) from entering the upper compartment 301 thus creating a concentrated liquid containing a high concentration of cells 305.

At the same time, a lower compartment 303 is dynamically formed and situated between the lower disc 115 and the dispenser end 109, which holds the concentrated liquid containing a high concentration of cells 305 proximate to the dispenser end 109.

The plunger 111 may be pushed downwards to any extent to achieve a desired volume of concentrated liquid containing a high concentration of cells 305, with the lower disc 115 effectively maintaining separation of the concentrated liquid containing a high concentration of cells 305 from the filtrate containing liquid 307 at all times.

Figure 4:
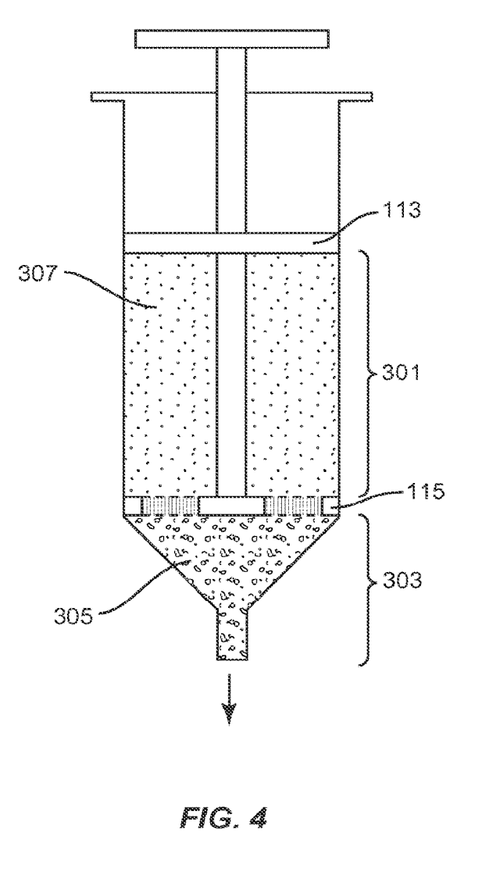
FIG. 4 illustrates a cross-sectional view of the exemplary filtration device of FIG. 3 in a concentrated cell expulsion mode according to an aspect of the present application.

A 'concentrated cell expulsion mode' will now be described. Once the desired volume of concentrated liquid containing a high concentration of cells 305 within the lower compartment 303 is achieved, the device may realize a 'concentrated cell or concentrated liquid expulsion mode' where there is a high concentration of cells wherein the cap 309 is removed and a downwards force is applied to the plunger 111 to cause at least the second disc 115 to be pushed downwards, e.g., as far as possible so as to abut the dispenser end 109. This results in the concentrated liquid containing a high concentration of cells 305 being expelled from the dispenser end 109, e.g., for administration to a treatment site. FIG. 4 illustrates a cross-sectional view of the exemplary filtration device of FIG. 1 in a concentrated liquid expulsion mode according to an aspect of the present application. In this way, high concentration of nucleated cells (e.g., eukaryotic cells, white blood cells, red blood cells, progenitor cells, stem cells, etc.) can be applied to a target tissue or to allograft material to enhance bone growth.

Figure 7:
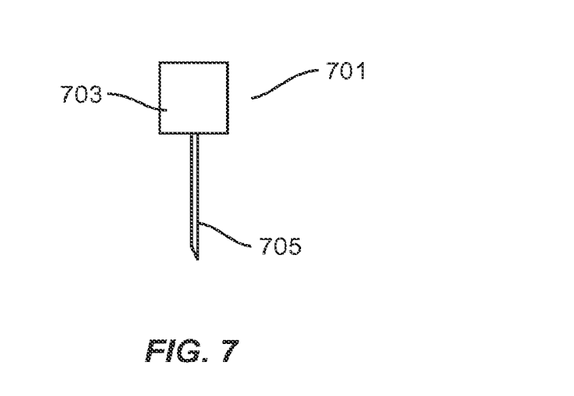
FIG. 7 illustrates a side view of an exemplary cannula according to an aspect of the present application.

FIG. 7 illustrates a side view of an exemplary cannula or needle 701 for use with a filtration device according to an aspect of the present application. The needle 701 may comprise a base 703 configured for attachment to the dispenser end 109, and a hollow needle 705 having any size or configuration adapted for effective flow of the therapeutically effective amount of desired concentrated liquid containing a high concentration of cells for administration to a treatment site, such as within a patient or to a bone defect or to hydrate allograft material.

According to various embodiments, a method for separating particulate matter (e.g., cells) from a liquid and administering same to a site will now be discussed. A housing is provided defining an elongate chamber disposed between a receiving end and a dispenser end. A plunger is slidably inserted within the chamber from the receiving end and an upper disc and a lower disc are provided each dependently or independently slidably affixed to the plunger, the lower disc facing the dispenser end and including at least one filter arrangement.

In one embodiment, the lower disc comprises a filter and moves dependently with the plunger. In this embodiment, the upper disc is configured to move independently of the plunger, for example, the upper disc can move in an upward direction toward the upper end as fluid pass through the lower disc and filter. The pressure from fluid will cause the upper disc to move away from the dispensing end and toward the upper end of the syringe.

In one embodiment, to achieve the 'start mode' the upper and lower discs may be moved downwards together towards the dispenser end and the dispenser end immersed in a liquid containing particulate matter (e.g., cells) desired to be concentrated.

In one embodiment, to achieve the 'aspiration mode,' the upper and lower discs are moved upwards together towards the receiving end for aspirating the liquid including particulate matter (e.g., cells) within the chamber.

In one embodiment, to achieve the 'filtration mode,' a removable cap is affixed to seal the dispenser end. The lower disc is moved downwards while the upper disc will move upward as fluid passes through the filter and the lower disc and contacts the upper disc. By forcing the plunger and lower disc in a downward direction, the liquid is forced to pass through the at least one filter arrangement of the lower disc. This results in dynamically forming an upper compartment and a lower compartment simultaneously, wherein the upper compartment is formed between the upper disc and the lower disc for containing the filtered liquid, and the lower compartment is formed between the lower disc and the dispenser end for containing the concentration cells and little or no liquid.

Once a desired volume of concentrated cells is attained, a 'concentrated cell or concentrated liquid expulsion mode' may be achieved by removing the cap and moving at least the lower disc downwards to abut the dispenser end, thus expelling the concentrated cells to the target tissue site or bone defect or they can be used to hydrate the allograft.

Alternate designs may be provided for providing and/or regulating filtration of fluid, including but not limited to types, placement, thickness and/or amount of filter media used, orientation of the filter arrangements, and so on.

Advantageously, a filtration device according to the present application comprises a minimum number of moving parts, minimizes complexity and is extremely user friendly, ultimately reducing the equipment and steps needed for achieving effective separation of particulate matter from a liquid to form a concentrated liquid and providing efficient delivery of a desired volume of the concentrated liquid to a site.

Cannula or Needle

The cannula or needle of the filtration device may comprise any size or configuration adapted for enabling effective flow of the therapeutically effective amount of desired concentrated liquid for administration to a treatment site or to the allograft material. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, nitinol, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey.

In various embodiments, the diameter of the cannula or needle is substantially the same throughout. In other embodiments, the diameter of the needle or cannula becomes smaller approaching the distal end.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient.

The thickness of the cannula or needle will also depend on the concentration of particulate matter in the liquid desired to be administered to the site or allograft. In various embodiments, the thickness includes, but is not limited to, from about 0.05 to about 1.655. The gauge of the cannula or needle may be the widest or smallest diameter or a diameter in between for insertion into a human or animal body. The widest diameter is about 14 gauge, while the smallest diameter is about 25 gauge. In various embodiments the gauge of the needle or cannula is about 17 to about 25 gauge.

In various embodiments, the plunger and/or cannula may include markings that indicate location at or near the site beneath the skin.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, surrounding the opening of the proximal end of the cannula or needle is a generally cylindrical hub having an engagement means (shown as internal threading) for engaging the dispensed end of the housing. Engagement means include, but are not limited to, threading, tracks, clips, ribs, projections, and the like that allow a secure connection between the housing and the proximal end of the cannula. For example, in various embodiments the engagement means may be a luer lock connection, where the cannula has mating threads that mate with the threads disposed on or in the housing.

Housing

The housing of the filtration device may be of various shapes including, but not limited to, cylindrical or tubular such that the housing defines a barrel or chamber which allows for slidable insertion of a plunger as well as the annular disc members there through.

The housing may comprise a variety of materials, such as, for example, polyurethane, polyurea, polyether(amide), PEBA, thermoplastic elastomeric olefin, copolyester, and styrenic thermoplastic elastomer, steel, nitinol, aluminum, stainless steel, titanium, metal alloys with high non-ferrous metal content and a low relative proportion of iron, carbon fiber, glass fiber, plastics, ceramics or combinations thereof.

Like the plunger, in various embodiments, the housing may have dose indicator markings (e.g., numbers, lines, letters, radiographic markers, etc.) to indicate, for example, the amount of liquid therein and the amount of concentrated liquid delivered.

The housing may have contours and allow easy grasping of the device during use. The housing can be angled for right and left hand users or can be generic for both hands.

Plunger

Although a first end of the plunger is shown as a handle, it will be understood that the knob can be a top, dial, or cap or any member that allows the user to utilize the plunger. In various embodiments, the plunger may comprise an elongate cylindrical rod which may be solid, have a hollow interior, or any combination thereof. Alternate shapes and configurations of the plunger may be contemplated.

The plunger has a diameter which fits within the respective holes of the first and second discs. The plunger may be longer than or the same size as the length of the housing of the syringe.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the amount of liquid delivered.

The plunger may be affixed to the first and second discs in various configurations to selectively enable movement of each of the first and second discs independently as well as in unison, in both upwards and downwards directions. In some embodiments, the plunger can be disposed in the center of the upper and/or lower disc and can be attached thereto by a rim. The rim can attach the upper disc to the plunger loosely so that the upper disc can slide in an upward direction toward the upper end when the device is in a filtration mode.

Filter Material

Filtration is commonly the mechanical or physical operation which is used for the separation of solids (e.g., cells) from fluids (liquids or gases) by interposing a medium through which only the fluid can pass. Oversize solids in the fluid are retained, depending on the pore size and filter thickness). Fluids flow through a filter due to a difference in pressure—fluid flows from the high pressure side to the low pressure side of the filter, leaving some material behind.

In various embodiments, with regards to the filter arrangement according to the present application the nature of the material used to make the filter arrangement, the compatibility of the materials chosen for the filter arrangement with one another and with the liquid to be processed are all factors which may be considered in selecting a particular material for a filter arrangement for a given application.

In various embodiments, the filter arrangement may comprise a unitary structure and/or a composite structure. The filter arrangement may include one or more portions having varying densities and/or pore size. For example, the filter arrangement may comprise a first portion having a density and/or pore size suitable to prevent the passage of cells there through and a second portion having a density and/or pore size suitable for passing the fluid there through.

In various embodiments, the filter arrangement may include various arrangements of porous media such as membranes, depth filters, and other porous media, and any combination thereof, suitable for preventing the passage of cells there through. Exemplary materials of the porous media may include polypropylene or high density polyethylene, porous plastics, or any combination thereof.

It should be noted that various types of porous arrangements can be used interchangeably with that of the present embodiment. While a polycarbonate membrane is especially suitable for use in a filtration device as disclosed herein, other porous membranes are also suitable.

The porous media may be configured to have any desired pore size. For example, exemplary pore sizes may include from about 0.1 or 0.5 to about 5.0 or 10.0 microns that will allow fluid flow to pass there through while preventing the passage of particulate matter.

As one skilled in the art will recognize, adjusting the pore size of the porous membrane and the porous depth filter in accordance with the type and/or size of matter to be collected permits the collection of the desired particulate matter. It is intended that the present disclosure should not be limited to a certain range of pore size.

One or more layers of porous media may be positioned in any fashion that functions to enable the desired filtration effect. As one skilled in the art will recognize, the porous arrangement may be variously configured and positioned as needed to achieve a particular result. For example, one or more layers of porous media may be separate, spaced apart, laminated together, integrally formed with and/or removably engaged with each other. In some embodiments, the filter may be continuous with the lower disc of the device. In some embodiments, the filter is disposed at discrete positions on the lower disc.

Liquid

As used herein, fluid or liquid refers to any fluid or liquid for which it may be desirable to collect a component of the fluid for the purpose of establishing its identity or presence in the fluid. In various embodiments, the component in the fluid will be a solid matter, such as particulate matter (e.g., cells). For example, the fluid may be air or gas, or a biological fluid, and it may be desirable to concentrate the number of cells in the biological fluid. In various embodiments, the biological fluid may be blood or bone marrow aspirate, and it may be desirable to concentrate the number of certain cells such as nucleated cells in the biological fluid.

Other exemplary fluids include but are not limited to body fluids, such as spinal fluid, amniotic fluid; bronchial lavage; sputum; fine needle aspirates; ground water; industrial processing fluids; electronic or medical dialysis fluids; to name just a few. It is intended that the present disclosure should not be limited by the type of fluid being processed.

A "therapeutically effective amount" is such that when administered, the concentrated liquid results in alteration of the biological activity, such as, for example, inhibition of inflammation, hydration of the treatment site, improvement in the condition, bone growth, etc. The dosage administered to a patient can be as single or multiple doses depending upon a variety of factors, including the liquid's pharmacokinetic properties, the route and/or location of administration, patient conditions and characteristics (sex, age, body weight, health, size, etc.), extent of symptoms, concurrent treatments, frequency of treatment and the effect desired.

Particulate Matter

As used herein, particulate matter refers to any substance in a fluid which is capable of collection. Exemplary particulate matter includes, but is not limited to cells (e.g., eukaryotic cells, white blood cells, red blood cells, progenitor cells, stem cells, etc.) or cell fragments, proteins, molecules, polymers, or the like. Specific exemplary biological matter includes red blood cells, white blood cells, stem cells, including distinguishing between nucleated and enucleated cells; cancer cells, including distinguishing between metastatic and normal cancer cells; proteins, nucleic acids, antibodies, or the like.

While a filtration device according to various aspects of the present disclosure can be used for any biological fluid, it is particularly useful for preparing concentrated liquids comprising nucleated cells that are beneficial for, e.g., bone and soft tissue repair.

It is intended that the present disclosure should not be limited by the type of matter being processed. In various embodiments, the fluid is blood or bone marrow aspirate and the particulate matter is a cell.

Sterilization

The filtration device components (e.g., cannula or needle, plunger, housing, discs, etc.) may be lightweight, disposable and sterilizable such that when the device is assembled, the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

In various embodiments, a kit is provided for separating particulate matter from a fluid, the kit comprising: a sterilized filtration device, comprising: a housing defining an elongate chamber disposed between a receiving end and a dispenser end; a plunger slidably inserted within the chamber from the receiving end; an upper disc and a lower disc each independently slidably affixed to the plunger, the lower disc facing the dispenser end and including at least one filter arrangement; and a removable cap affixed to the dispensing end.

In various embodiments, a kit is provided which may include additional parts along with the filtration device combined together to be used to prepare and administer the therapeutically effective amount of concentrated liquid. The kit may include the filtration device in a first compartment. The second compartment may include a needle or cannula, and any other instruments needed for the administration of the concentrated liquid. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

The device and method may be used to treat a bone repair site, e.g., one resulting from injury, defect brought about during the course of surgery, infection, malignancy or developmental malformation, which requires mechanical support. The device and method can be utilized in a wide variety of orthopedic, periodontal, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g., deficit filling, discectomy, laminectomy, excision of spinal cord tumors, anterior cervical and thoracic operations, repairs of spinal injuries, scoliosis, lordosis and kyphosis treatments, intermaxillary fixation of fractures, mentoplasty, temporomandibular joint replacement, alveolar ridge augmentation and reconstruction, onlay bone grafts, implant placement and revision, sinus lifts, etc. Specific bones which can be repaired or replaced with the device herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones. The device can be implanted at the bone repair site, if desired, using any suitable affixation means, e.g., sutures, staples, bioadhesives, or the like.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more therapeutically effective doses to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for separating particulate matter from a liquid comprising:
   providing a housing defining an elongate chamber disposed between a receiving end and a dispenser end;
   providing a plunger slidably inserted within the chamber from the receiving end;
   providing an upper disc having a hole slidably receiving the plunger and a lower disc, the lower disc being fixed to an end of the plunger below the upper disc, the lower disc facing the dispenser end and including at least one filter arrangement;
   introducing the liquid into the chamber by sliding the upper and lower discs upwards towards the receiving end, the liquid including particulate matter;
   affixing a cap to the dispensing end; and
   separating the liquid from the particulate material by filtering the liquid through the at least one filter arrangement of the lower disc by sliding the lower disc downwards to separate the particulate matter from the liquid in the chamber so as to cause the upper disc to slide toward the receiving end.

2. A method of claim 1, wherein the method further comprises removing the cap and sliding the upper disc downwards to achieve a concentrated liquid expulsion mode.

3. A method of claim 2, wherein the upper compartment is formed between the upper disc and the lower disc and the lower compartment is formed between the lower disc and the dispenser end.

4. A method for separating particulate matter from a liquid comprising:
   providing a filtration device comprising: an elongated housing having at least one wall defining a chamber disposed between a receiving end and a dispensing end including an outlet to dispense; a plunger slidably inserted within the chamber from the receiving end; a first impermeable disc having a hole slidably receiving the plunger, said first impermeable disc being slidably and sealingly moveable along a length of said plunger, and being slidably and sealingly movable along a length of said at least one wall defining said chamber; and a second disc including at least one filter, said second disc being fixed to an end of the plunger and located between the first impermeable disc and said dispensing end, said second disc being slidably and sealingly movable along a length of said at least one wall defining said chamber, wherein, the shape of said discs substantially conforms to the shape of said chamber, wherein a liquid including particulate matter is disposed in the chamber; and sliding the second disc downwards to achieve a filtration mode for separating the particulate matter from the liquid so as to cause the first disc to slide toward the receiving end.

5. A method of claim 4, wherein the elongated housing comprises a tubular barrel defining a cylindrical chamber.

6. A method of claim 4, wherein the second disc comprises a frame having an annular periphery forming a slidable seal with said at least one wall of said chamber.

7. A method of claim 6, wherein said frame includes a plurality of arms defining at least one void.

8. A method of claim 7, wherein said at least one filter is disposed within, above or below said at least one void or said at least one filter rests on or is attached to the top or bottom of said plurality of arms.

9. A method of claim 4, further comprising a cap removably affixed to said dispensing end to close said outlet.

* * * * *